United States Patent [19]

Bonaldo

[11] Patent Number: 5,154,703
[45] Date of Patent: Oct. 13, 1992

[54] BLOODLESS CATHETER

[75] Inventor: Jean M. Bonaldo, Upland, Calif.

[73] Assignee: Care Medical Devices, Inc., Ontario, Calif.

[21] Appl. No.: 606,048

[22] Filed: Oct. 30, 1990

[51] Int. Cl.$^5$ .............................................. A61M 5/00
[52] U.S. Cl. .................................. 604/244; 604/202; 604/88; 604/905
[58] Field of Search ........................ 604/82, 83, 86–88, 604/164, 167, 169, 192, 198, 205, 240, 241, 244, 905

[56] References Cited

U.S. PATENT DOCUMENTS

| | | | |
|---|---|---|---|
| 3,986,508 | 10/1976 | Barrington | 604/905 X |
| 4,019,512 | 4/1977 | Tenczar | 604/905 X |
| 4,457,749 | 7/1984 | Bellotti et al. | 604/29 |
| 4,512,766 | 4/1985 | Vailancourt | 604/169 |
| 4,781,702 | 11/1988 | Herrli | 604/244 |
| 4,874,377 | 10/1989 | Newgard et al. | 604/167 |
| 4,917,668 | 4/1990 | Haindl | 604/167 |
| 4,981,469 | 1/1991 | Whitehouse et al. | 604/86 |
| 4,998,921 | 3/1991 | Vickroy et al. | 604/167 |

FOREIGN PATENT DOCUMENTS 9007953  7/1990  PCT Int'l Appl. ............ 604/905 X Primary Examiner—C. Fred Rosenbaum
Assistant Examiner—Adam J. Cermak
Attorney, Agent, or Firm—Robert R. Thornton

[57] ABSTRACT

A medical device which presents the backflow of fluid therethrough is particularly useful as a bloodless catheter assembly, that is, prevents the backflow of blood through the catheter by utilization of a self-closing valve carried in a hollow catheter housing to one end of which a catheter is fixed so as to provide a fluid passage through the catheter and catheter housing. The fluid passage in the catheter housing is sealed by a self-sealing valve element extending transversely across the passage upstream from the catheter. A hollow needle is held in the catheter housing downstream of and pointed at the valve element. Attachment of a fluid dispensing medical appliance to the other catheter housing end forces the valve element downstream onto the needle so as to pierce the valve element and open a fluid passage from the catheter housing upstream of the valve element through the hollow needle to the catheter. Removal of the medical appliance permits the resiliently biased valve element to move upstream away from the needle, thereby resealing and thus reclosing the fluid passage which extends through the hollow needle.

10 Claims, 1 Drawing Sheet

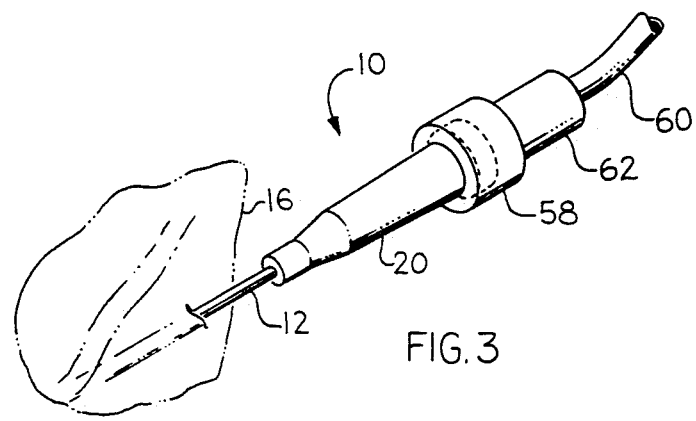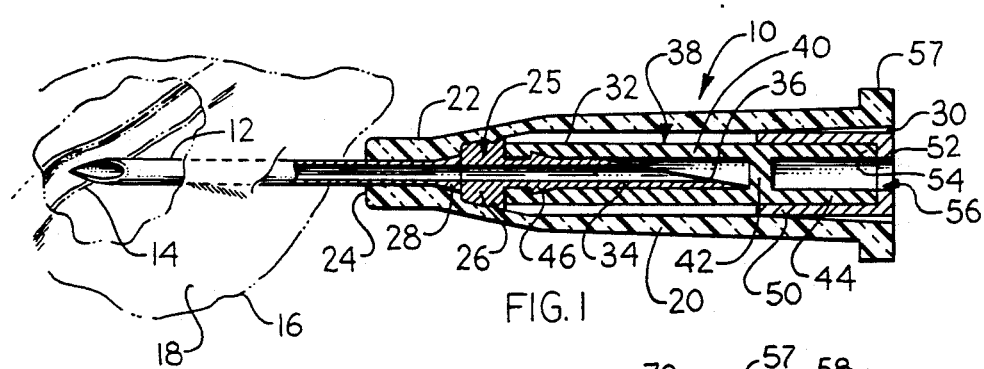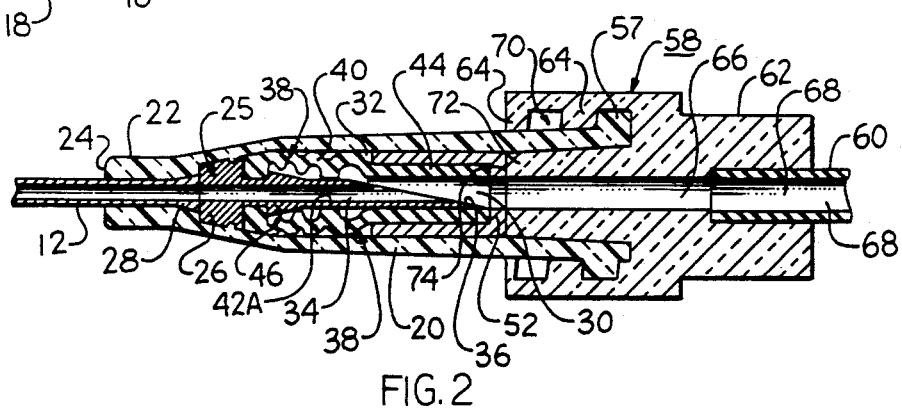

BLOODLESS CATHETER

BACKGROUND OF THE INVENTION

The present invention relates to a catheter for use in the practice of medicine.

Catheters have long been utilized in medical practice and are designed for insertion into blood vessels and similar passageways or cavities in the body, to permit infusing or withdrawing fluids or to maintain the openness of an existing passageway into the existing vessel or cavity for subsequent infusion or withdrawal of fluids. The catheter is normally mounted on a cannula for insertion into the body and, when the cannula has pierced the vessel or cavity, the catheter is moved into position so as to maintain the opening when the cannula is withdrawn.

My U.S. Pat. No. 4,917,669 utilizes a novel catheter inserter construction to avoid transmission of infection due to contact by the medical personnel with contaminated blood on a cannula used to insert the catheter. In this patent, a housing completely encloses the cannula after the catheter-carrying cannula, which has been inserted into the patient's vein, is retracted into the housing, leaving the catheter in place. The catheter inserter is then removed from the catheter assembly. However, conventionally, when the cannula is removed, the catheter permits blood from the vein to flow back through the catheter and out onto the patient, bedding, etc., thereby potentially contaminating materials to be handled by others, as well as creating aesthetic problems. This problem may be minimized during the removal of the cannula from the catheter by one of the attendant medical personnel placing a finger on the catheter at the point where the catheter enters the skin, or slightly there beyond, so as to stop the flow of blood manually while the cannula is withdrawn. However, removal of the pressure will permit the subsequent backflow of blood through the catheter.

U.S. Pat. No. 4,894,052 describes a catheter in which this problem exists. In the device shown in U.S. Pat. No. 4,894,052, it is necessary to apply the pressure on the catheter in order to prevent the back flow of blood through the device after a cannula-carrying plug, which has been inserted into the holder for the catheter, is withdrawn from the patient's vein to withdraw the cannula, while an appropriate medical device, such as a fluid transmission line by which the fluid to be infused in the patient's vein, is being connected to the catheter holder at the open end by means of complementary luer-type fittings. See column 7, lines 11–16, 65–66, and column 8, lines 30–41 thereof. However, this procedure is somewhat difficult, since the attendant is required to maintain the pressure on the catheter to prevent back flow with one hand at the same time that the luer fittings are being mated with each other, or, alternatively, two attendants are required, one to mate the luer fittings and the other to apply the pressure on the catheter to stop the blood flow.

An early attempt to solve this problem is illustrated in U.S. Pat. No. 3,915,168, in which a resealable rubber or plastic tube is used for connecting the fluid administration apparatus to the catheter. The tube is bent so as to permit the insertion of the cannula through the side wall of the tube into the catheter to the puncture the vein. The cannula is then withdrawn from the vein through the sidewall of the tube, the tube resealing upon withdrawal. However, this device does not contemplate protection of the contaminated needle after withdrawal, and requires a certain amount of manual dexterity and skill in order to cause the needle, when inserted through the flexible tubing, to pass through the small central bore in the catheter carrying hub to enter the catheter.

U.S. Pat. No. 4,842,591 illustrates a catheter assembly intended to avoid this problem. This device has a catheter housing through which a fluid passage extends. A resilient septum with a preformed slit is mounted in the fluid passage so as to seal the passage. When a syringe is inserted into the catheter housing, a movable annular plug, which is disposed upstream from the septum, is engaged by the syringe so as to be forced downstream against the septum, thereby opening the septum slit to permit the passage therethrough of the liquid expelled from the syringe. Upon withdrawal of the syringe, the septum resiliency returns the annular plug to its original upstream position, so as to permit the septum slit to seal. This device suffers inherently in having a preformed slit, which may be subject to leakage, in addition to presenting difficulties in its economical manufacture by reason of the two-section housing utilized in order to accommodate the disk-shaped septum. Utilizing an annular plug to open the preformed septum slit appears to require the substantial thickness of the septum illustrated in U.S. Pat. No. 4,842,591 to provide the resiliency necessary for the closure of the septum slit upon removal of the syringe. Thus, a septum slit design appears to be inherently susceptible to leakage through the slit, particularly in repetitive use.

In U.S. Pat. No. 4,657,536, there is shown a catheter having a check valve-type termination, intended specifically for use with implanted infusion pumps and the like, where substantially high fluid pressure is generated. In this device, the catheter tip is plugged by a solid plug, and a bore form transversely there across upstream of the plug. An elastic sleeve encloses the catheter tip so as to seal the transverse bore. When inserted in the patient, the elastic sleeve prevents back flow, while permitting forward flow when the fluid is sufficiently pressurized to expand the sleeve. However, this type of device is not suited for use as an intravenous catheter, since the catheter tip is plugged, thereby precluding the insertion of the cannula through the catheter for use in insertion of the catheter into the patient's vein.

BRIEF DESCRIPTION OF THE INVENTION

According to the present invention, a catheter assembly includes a housing having a longitudinal passageway extending therewithin between an upstream end and a downstream end thereof and which has a catheter tube extending outwardly from its downstream end in fluid communication with said longitudinal passageway. A hollow needle is mounted in said longitudinal passageway in proximity to the housing downstream end so as to be upstream of and provide a fluid passageway with the catheter tube, the needle terminating in a needle point which points toward the housing upstream end and terminates short thereof. Valve means, which is disposed in the housing longitudinal passageway between the housing downstream end and the housing upstream end, includes a valve element which is made of material which is self-sealing after puncture by the needle point and is disposed transversely in the longitudinal passage between the needle point and the housing upstream end, so that the valve means normally closes the fluid passageway extending through the catheter and the hollow needle upstream of the needle point at the valve element. The valve means includes a valve actuator which is slidably disposed within the longitudinal passageway so as normally to be adjacent the housing upstream end and which is operable when moved longitudinally from its normal disposition toward the housing downstream end by the attachment of a medical appliance to the housing upstream end to urge the valve element against the needle point and onto the needle after being punctured by the needle point, whereby the fluid passageway normally terminating at the valve element extends through the valve element so as to provide direct fluid communication between the housing upstream end and the catheter when the valve element is pierced by the needle point, thereby permitting fluid contained in the medical appliance to flow through the housing to the catheter tube. The valve element is resiliently mounted with respect to the needle point, so that when the medical appliance is removed from the catheter assembly, the valve element moves upstream of the needle point and seals the puncture so as to again close the fluid passageway extending through the catheter tubing and the hollow needle at the valve element.

BRIEF DESCRIPTION OF THE DRAWING

The present invention may be more readily understood by reference to the accompanying drawing, in which:

FIG. 1 is a right side elevational view, in section, of a bloodless catheter according to the present invention prior or subsequent to use;

FIG. 2 is a view of the device of the present inventor, as shown in FIG. 1 when in use; and FIG. 3 is an isometric view of the bloodless catheter of the present invention while in use.

DESCRIPTION OF THE PREFERRED EMBODIMENT

Referring now to FIG. 1, there is shown a right side elevational view, partially in section, of a catheter assembly 10 according to the present invention. The catheter assembly 10 includes a catheter 12 of conventional construction, which may be any conventional catheter tubing material, extending into a vein 14 through the skin 16 and flesh 18 of a patient. For purposes of description, a vein is shown. However, it will be understood that the catheter assembly of the present invention may be utilized in any of the various applications for which catheters are used in the medical profession. The catheter 12 extends into a catheter housing 20 at one end 22 thereof, which is the downstream end, through a bore 24 formed in the downstream end 22. The catheter terminates within the downstream end 22 at a needle assembly 25 which includes a needle hub 26 which abuts the catheter 12 at an enlarged catheter termination recess 28. The recess 28 serves to hold the catheter in place within the housing 20.

The catheter housing 20 has an open upstream end 30 at the opposite end of the catheter housing 20 from the downstream end 22. The downstream end bore 24 extends from the downstream end 22 upstream toward the upstream end 30 and opens into an enlarged central passage 32. The central passage 32 extends from the bore 24 to the upstream end 30. In the presently preferred embodiment, the central passage 32 gently tapers inwardly from the open upstream end 30 toward the needle hub 26. The needle hub 26 has a hollow needle 34 extending upstream therefrom and terminating in a needle point 36. A valve assembly 38 is disposed in the central passage 32 upstream from the needle hub 26 and terminates adjacent the upstream housing end 30.

As will be seen in FIG. 1, the hollow needle 34 is coaxially disposed within a first sleeve 40 of the valve assembly 38. The first sleeve 40 terminates in a valve element 42 which extends transversely across the bore of the first sleeve 40 so as to close a fluid passage through the catheter 12 and the hollow needle 34. The valve assembly 38 has a second sleeve 44 which extends from adjacent the upstream end 30 of the housing 20 to the valve element 42.

The valve assembly 34 is fixed to the needle hub 26 by an annular conical rim 46 formed on the exterior of the hollow needle 34 between the needle hub 26 and the point 36 so as to engage the interior surface of the first sleeve 40, thereby fixing the sleeve 40 in position with respect to the hub 26. If desired, a complementary conical recess can be formed in the first sleeve 40 although, in many embodiments, the sleeve, upon being extended over the annular rim 46, will be sufficiently fixed to the needle 34 to insure the adequacy of the retention of the first sleeve 40 on the needle 34 adjacent the needle hub 26.

A valve actuator 50 is disposed within the upstream housing end 30 so as to be generally coterminous therewith and extend downstream into the central passage 32 so as to terminate adjacent the valve element 42. The valve actuator 50 is seen in FIG. 1 to be coaxially disposed about the second sleeve 44 and has a base 52 which engages the upstream end 54 of the second sleeve. The base portion 52 has an aperture 56 formed therein so as to provide a fluid passage downstream from the upstream end 30 which is sealed by the valve element 42, just as the fluid passage upstream from the catheter 12 through the needle 34 is sealed by the opposite side of the valve element 42. The valve actuator 50 is fixed to the second sleeve 44 by any conventional means (not shown) such as an adhesive, heat fusion, or structure similar to that of the cannula rim 46.

The needle hub 26 is press-fit into the housing 20 in a locking recess formed in the central passage so as to be complementary to the outer periphery of the needle hub 26, and so the needle 34 fixed in the housing 20. The valve assembly 38 is therefore also fixed in longitudinal coaxial alignment with the needle 34 within the central passage 32. Thus, the valve actuator 50, valve assembly 38, hollow needle 34 and housing downstream end bore 24 are all axially aligned with one another so as to provide a cylindrical fluid passageway from the housing downstream end 24 to the housing upstream end 30 which is sealed by the valve element 42.

The valve element 42, and in the preferred embodiment the valve sleeves 40 and 44, are all formed of a resilient elastic material such that, when the needle point 36 pierces the valve element 42 and is then withdrawn therefrom, the valve element 42 reseals so as to seal the aforementioned cylindrical longitudinal fluid passage against the passage of fluid therethrough either from the upstream end 30 or the downstream end 24. The housing 20 terminates, at the upstream end, and an enlarged flange portion 57 which, in the preferred embodiment is suitable for mating with the luer-type fitting in general use in the medical profession for connecting medical appliances to one another in a fixed relationship.

Referring now to FIG. 2, the device of FIG. 1 as shown, but with a medical appliance 58 attached thereto. For purposes of explanation, the medical appliance 58 is a simple I V tube 60 which terminates in an I V tube luer-type locking fitting 62. As will be seen in FIG. 2, the locking fitting 62 has a series of spiral teeth 64 onto which the flange portion 57 has been threaded so as to form a fluid-tight fit between the catheter assembly 10 and the medical appliance 58. The locking fitting 62 has a bore 66 formed therewithin which communicates directly with a bore 68 in the I V tube 60. The spiral teeth 64 are formed within a hollow recess 70 in the locking fitting 62. The locking fitting 62 has a central tapered annular stem 72 extending therefrom within the recess 70, through which the fitting bore 66 extends. The stem 72 terminates in an annular face 74.

As is shown in FIG. 2, the annular stem face 74 has engaged the base 52 of the valve actuator 50, so as to force the valve actuator 50 and the valve assembly second sleeve 44 downstream toward the needle hub 26. The valve element 42 has therefore been pierced by the needle point 36 so is configured as an annulus 42A which forms a seal about the needle 34. The valve assembly first sleeve 40 is seen to have expanded outwardly and contracted longitudinally in response to the pressure exerted on the valve actuator base 52 by the threading onto the housing flange 56 of the luer-type fitting 62 to permit the valve element 42 to be moved downstream onto the needle 34. Thus, when the luer-type fitting 62 is locked to the flange 56 of the housing 20 as shown in FIG. 2, a fluid passage extends through the catheter 10, the needle hub 26, the needle 34, the valve assembly second sleeve 44, and the valve actuator base aperture 56 into the annular stem 72 of the medical appliance 58.

When the locking fitting 62 is removed from the housing flange 56, the resiliency of the first sleeve 40 will cause the valve element 42 to move back upstream of the needle point 36 to the disposition shown in FIG. 1, thereby again sealing the fluid passage through the catheter at the valve element 42 to preclude blood from flowing back through the catheter and out the catheter housing upstream end 30, without the necessity of finger pressure on the catheter. The catheter assembly 10 can be left in this disposition without the danger of backflow of blood for an indefinite period without the necessity of plugging the upstream end 50 of the housing 20. When another medical appliance is to be attached to the catheter assembly 10, its luer-type fittings are mated onto the flange 56, without the necessity of finger pressure on the catheter 12 to prevent backflow of blood.

The valve assembly 38 has been described heretofore in a particular embodiment specifically adapted for use in a bloodless catheter. However the valve assembly 38, and accompanying components, may be generally used in the medical field for various fluid transfer applications. Consequently, the present invention, in its broadest implementation, is not limited to use in a bloodless catheter. The various components of the bloodless catheter are molded from conventional medical grade plastics For example, the first sleeve 40, valve element 42, and second sleeve 44 may be molded as a unitary piece of medical grade latex, such as 7377-30 gum formulated to 80 Shore A durometer hardness, formulated and molded by West Company of Philadelphia, Pa. The valve actuator 50 may be injection molded from medical grade polypropylene, such as grade PD-626 Profax ® polypropylene distributed by Himont U.S.A., Inc. of Wilmington, Del. The catheter housing 20 may also be made of medical grade polypropylene. The needle hub 26 and needle 34 may be injection molded as a single piece of medical grade polycarbonate, such as from Calibre ®200-15 polycarbonate resin manufactured by Dow Chemical Company of Midland, Mich. The foregoing materials are described by way of example only, and are not intended to constitute limitations upon the practice of the present invention, as defined in the following claims.

The invention claimed is:

1. A medical assembly comprising:

a housing having a longitudinal passageway extending therewithin between an upstream end and a downstream end thereof;

hollow needle means mounted in said longitudinal passageway so as to be upstream of and in fluid communication with said downstream end, said needle means including a hollow needle terminating in a needle point which points toward the housing upstream end and terminates short thereof, whereby a fluid passageway is provided from said housing downstream end upstream through said hollow needle;

valve means disposed within said passageway between said upstream end and said downstream end so as to normally close said passageway upstream from said needle point;

valve engaging means for engaging said valve means downstream from said needle point and operable to fix said valve means to said needle means, said valve means including a first hollow cylindrical element coaxially disposed within the passageway and which is engaged by said valve engaging means, a second hollow cylindrical element axially aligned with the first cylindrical element and disposed between said first cylindrical element and said housing upstream end and terminating at one end adjacent to the upstream end, and a valve element connected between the first cylindrical element and the second cylindrical element so as to be normal to the axes thereof, thereby closing a cylindrical interior passage extending through the first and second cylindrical elements, said valve element being made of a material which is self-sealing after puncture by said needle; and valve actuator means slidably disposed within the longitudinal passageway adjacent the valve means and operable when actuated by being moved longitudinally from its normal disposition toward the housing downstream to urge the valve element downstream onto the needle after being pierced by the needle point, whereby the fluid passageway normally terminating at the valve element extends through the valve element so as to be in direct fluid communication with the housing upstream end.

2. The apparatus of claim 1, and in which the actuator means is resiliently biased so as to return to its normal disposition when deactuated, and in which the valve element is operable to reseal said passageway upstream of the needle point upon deactuation of the actuator means.

3. Apparatus according to claim 2, and including catheter tubing means extending outwardly from the housing downstream end and fixed thereto so that said fluid passageway extends through the catheter tubing means, whereby said catheter tubing means is in fluid communication with said hollow needle through said housing downstream end.

4. A medical assembly comprising:

a housing having a longitudinal passageway extending therewithin between an upstream end and a downstream end thereof;

needle means mounted in said longitudinal passageway in proximity to said housing downstream end so as to be upstream of and in fluid communication therewith, said needle means including a hollow needle terminating in a needle point which points toward the housing upstream end and terminates short thereof, whereby a fluid passageway is provided through said housing downstream end and through said hollow needle; and valve means disposed within said passageway between said upstream end and said downstream end so as to close said passageway upstream from said needle point, and in which said needle means includes valve engaging means for engaging said valve means between said needle point and said downstream end so as to hold said valve means to said needle means, said valve means including a first hollow cylindrical element coaxially disposed within the passageway and which is engaged by said valve engaging means, a second hollow cylindrical element axially aligned with the first cylindrical element and disposed between said first cylindrical element and said housing upstream end and terminating at one end adjacent to the upstream end, and a valve element connected between the first cylindrical element and the second cylindrical element so as to be normal to the axes thereof, thereby closing a cylindrical interior passage extending through the first and second cylindrical elements, said valve element being made of a material which is self-sealing after puncture by said needle, said valve means including valve actuator means slidably disposed within the longitudinal passageway so as normally to be adjacent the housing upstream end and operable when moved longitudinally from its normal disposition toward the housing downstream end to urge the valve element onto the needle after being pierced by the needle point, whereby the fluid passageway normally terminating at the valve element extends through the valve element so as to be in direct fluid communication with the housing upstream end when the valve element is pierced by the needle point.

5. Apparatus according to claim 4, and in which the longitudinal passageway has an overall inward taper between the upstream end and the downstream end.

6. Apparatus according to either of claims 4 or 5, and in which said needle means includes a needle hub enclosing said hollow needle, by which said hollow needle is mounted in said passageway, said needle hub closing said longitudinal passageway to the flow of fluid except through said hollow needle.

7. Apparatus of claim 6, and including catheter tubing means extending outwardly from the housing downstream end housing and fixed thereto so that said fluid passageway extends through the catheter tubing means, whereby said catheter tubing means is in fluid communication with said hollow needle through said housing downstream end.

8. A catheter assembly comprising:

a housing having a central passageway extending between an upstream housing end of a first diameter and a downstream housing end of a second diameter less than the first diameter;

needle means mounted in said passageway and having a needle hub fixed to said housing in proximity to said downstream end and including a hollow needle which is pointed upstream from the hub so as to be axially aligned in said passageway so as to form an aperture extending through the hub;

valve means disposed within said passageway between said upstream end and said hub so as to close said passageway upstream from said hub, and in which said needle means includes valve engaging means for engaging said valve means adjacent said hub so as to hold said valve means to said needle means, said valve means including a first hollow cylindrical element coaxially disposed within the passageway and which is engaged by said valve engaging means, a second hollow cylindrical element axially aligned with the first cylindrical element and disposed between said first cylindrical element and said housing upstream end and terminating at one end adjacent to the upstream end, and a valve element connected between the first cylindrical element and the second cylindrical element so as to be normal to the axes thereof, thereby closing a cylindrical interior passage extending through the first and second cylindrical elements, said valve element being made of a material which is self-sealing after puncture by said needle;

guide means disposed in said central passageway so as to enclose said valve means second element, said guide means having a hollow cylindrical element which is coaxially disposed within the housing with respect to the valve means second element, and a base element, normal to the coaxially disposed element, which engages said end of the valve means second element adjacent the housing upstream end, said guide means base element having an aperture formed therein so as to be coaxially aligned with the valve means interior passage; and catheter tubing means fixed to the housing downstream end so as to be coaxially disposed in the central passageway and extend out of the housing downstream end.

9. A catheter assembly comprising:

a longitudinally tapered housing of circular cross-section and having a longitudinal passageway generally of circular cross-section extending between an upstream housing end of a first diameter and a downstream housing end of a second diameter which is less than the first diameter, said housing and passageway tapering generally in the same direction;

needle means fixed to said housing in said passageway and having a needle hub disposed in proximity to said downstream end through which a hollow needle extends so as to be axially aligned with passageway and point toward said upstream end;

valve means disposed within said passageway between said upstream end and said hub so as to enclose said needle and including a first hollow cylindrical element coaxial about the needle in the passageway, a second hollow cylindrical element axially aligned with the first cylindrical element and dispose between said first cylindrical element and said housing upstream end and terminating adjacent to the upstream end, and a valve element connected between the first cylindrical element and the second cylindrical element so as to be normal to the axes thereof, thereby closing a cylindrical interior passage extending through the first and second cylindrical elements, said valve means being made of a material which is self-sealing after puncture by said needle;

engaging means for fixing said valve means to said needle means adjacent said hub;

guide means disposed about said valve means second element so as to be coaxial therewith, said guide means having a hollow coaxial element which is coaxially disposed within the housing with respect to the valve means second element, and a base element, normal to the coaxial element, which closes one end of the coaxial element adjacent the housing upstream end, said guide means base element having an aperture formed therein so as to be axially aligned with the valve means interior passage; and catheter tubing means coaxially disposed in the central passageway downstream of the hub and extending out of the housing downstream second end.

10. A catheter assembly comprising:

a longitudinally tapered housing of circular cross-section and having a longitudinally tapered central passageway extending between an upstream housing end of a first diameter and a downstream housing end of a second diameter less than the first diameter, said housing and passageway tapering generally in the same direction;

needle means mounted in said passageway and having a needle hub fixed to said housing within said passageway in proximity to said downstream end through which a hollow needle extends so as to be axially aligned in said passageway and extend toward said upstream end;

valve means disposed within said passageway between said upstream end and said hub so as to enclose said needle, said needle means including valve engaging means for fixedly engaging said valve means adjacent said hub so as to hold said valve means to said needle means, said valve means including a first hollow cylindrical element coaxial with the passageway and which is engaged by said valve engaging means, a second hollow cylindrical element axially aligned with the first cylindrical element and disposed between said first cylindrical element and said housing upstream end and terminating adjacent to the upstream end, and a valve element connected between the first cylindrical element and the second cylindrical element so as to be normal to the axes thereof, thereby closing a cylindrical interior passage extending through the first and second cylindrical elements, said valve means being made of a material which is self-sealing after puncture by said needle;

guide means disposed between said valve means second element and said housing upstream end so as to be coaxial therewith and extend into said central passageway to enclose said valve means second element adjacent said housing first end, said guide means having a hollow coaxial element which is cylindrical and which is coaxially disposed within the housing with respect to the valve means and a second element, normal to the coaxial element, which closes one end of the coaxial element adjacent the housing upstream end, said guide means second element having an aperture formed therein so as to be coaxially aligned with the valve means interior passage; and catheter tubing means fixed to the housing so as to be coaxially disposed in the central passageway and extend out of the housing downstream end.

* * * * *